US00PP24633P2

(12) United States Plant Patent
Kordes

(10) Patent No.: US PP24,633 P2
(45) Date of Patent: Jul. 15, 2014

(54) SHRUB ROSE PLANT NAMED 'KORCHAKON'

(50) Latin Name: *Rosa hybrida*
Varietal Denomination: KORchakon

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 79 days.

(21) Appl. No.: 13/507,406

(22) Filed: Jun. 26, 2012

(51) Int. Cl.
*A01H 5/00* (2006.01)

(52) U.S. Cl.
USPC ..... Plt./107; Plt./101; Plt./102

(58) Field of Classification Search
USPC ..... Plt./101, 102, 107
See application file for complete search history.

*Primary Examiner* — Susan McCormick Ewoldt

(57) ABSTRACT

A new and distinct variety of rose with novel light pink flowers and attractive foliage with excellent disease resistance. It exhibits spreading growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORchakon'.

CROSS REFERENCES AND FEDERAL R&D STATEMENT

There are no cross referenced or related applications. This variety was developed without the aid of any research grant.

The new variety of rose plant of the present invention originated from a controlled crossing in a breeding program of two distinct parents during the summer of 1999. The crossing was between an 'un-named seedling', the seed parent, and another 'un-named seedling', the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORchakon'.

SUMMARY OF THE INVENTION

The new rose plant may be distinguished from its seed parent, an 'un-named seedling', by the following combination of characteristics:

1. 'KORchakon' has light pink flowers with a semi-double petal count, whereas the 'un-named seedling' has red flowers with a single petal count.
2. 'KORchakon' has a compact, spreading growth habit, whereas the 'un-named seedling' has a compact, yet upright, growth habit.

The new rose plant may be distinguished from its pollen parent, an 'un-named seedling', by the following combination of characteristics:

1. 'KORchakon' has small, light pink flowers, whereas the 'un-named seedling' has medium sized, pink/cream flowers.
2. 'KORchakon' has better disease resistance than the 'un-named seedling'.

The objective of the hybridization was to create a new and distinct rose plant with unique qualities, such as:

1. Uniform growth and flowering;
2. Abundant attractive, recurrent pink flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORchakon' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORchakon' was selected in May, 2000 from the seedling beds to be asexually propagated for further evaluation. The first asexual propagation of 'KORchakon' was done by budding to seedling understocks in July, 2000 at the inventor's nursery in Offenseth-Sparrieshoop, Germany.

This initial and other subsequent propagations conducted in controlled environments demonstrate that 'KORchakon' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORchakon'.

DETAILED BOTANICAL DESCRIPTION

The following is a description of 'KORchakon', as observed growing in October, 2011 in a nursery in Jackson County, Oreg. on plants 2 years of age. Color references are made using The Royal Horticultural Society (London, England) Colour Chart, 2001 except where common terms of color are used.

For a comparison, several physical characteristics of the rose variety 'KORtufee', a rose variety from the same inventor described and illustrated in U.S. Plant Pat. No. 16,849 and issued on Jul. 18, 2006 are compared to 'KORchakon' in Chart 1.

CHART 1

| Characteristic | 'KORchakon' | 'KORtufee' |
|---|---|---|
| Stamen count | 50-60 | 30 |
| Mature prickle color | Green-Yellow Group 161C | Greyed-Red Group 181D |
| Petal count | 25-30 | 45-55 |

Parents:

*Seed parent*.—'Un-named Seedling'.

*Pollen parent*.—'Un-named Seedling'.

Classification:

*Botanical classification*.—*Rosa hybrida* 'KORchakon'.

*Commercial classification*.—Shrub rose.

FLOWER AND FLOWER BUD

Blooming habit: Recurrent.

Flower bud:

*Size*.—Upon opening, 12 mm in length from base of receptacle to distal end of bud and 12 mm diameter at its widest point.

*Bud form*.—Short. Globular.

*Bud color*.—As sepals first unfold, bud color is Red Group 52C with a basal petal zone of Yellow Group 8D. When ¼ open, the upper surface of petals is Red-Purple Group 63D, infused with Red-Purple Group 62A, and the lower surface is Red-Purple Group 65B with intonations of Red-Purple Group 61D and a basal petal zone of White Group N155C.

*Sepals*.—Color: Upper surface: Yellow Group 146D. Lower surface: Yellow-Green Group 144C. Size: Average 10 mm (l)×5 mm (w). Shape: Weak foliaceous appendages on three of the five sepals. Apex: Apiculate. Base: Flat at union with receptacle. Quantity: Five. Surface texture: Upper side: Pubescent with stipitate glands. Lower surface: Lightly pubescent with stipitate glands. Margins: Pubescent.

Receptacle:

*Surface*.—Smooth.

*Color*.—Yellow-Green Group 144B.

*Shape*.—Urn-shaped.

*Size*.—8 mm (h)×4 mm (w).

Peduncle:

*Surface*.—With stipitate glands.

*Length*.—25 to 40 mm average length.

*Diameter*.—1.5 to 2 mm average diameter.

*Color*.—Yellow-Green Group 146D.

*Strength*.—Strong.

*Borne*.—Multiple flower buds per stem, generally 2 to 5.

Flower bloom:

*Fragrance*.—None.

*Duration*.—On the plant 3 to 4 days. As a cut flower, 3 to 4 days. Senesced petals drop away cleanly.

*Size*.—Small for a shrub rose. When open, the average flower diameter is 40 mm and the average flower height is 20 mm.

*Form*.—Shape of flower when viewed from the side: Upon opening, upper part: Flattened convex. Upon opening, lower part: Concave. Open flower, upper part: Flattened convex. Open flower, lower part: Concave.

Color:

*Upon opening, petals*.—Outermost petals: Outer Side: White Group N155C. Inner Side: Red-Purple Group N57C, with White Group N155D in the basal petal zone. Innermost petals: Outer Side: White Group N155C. Inner Side: Red-Purple Group N57C, with White Group N155D in the basal petal zone.

*Upon opening, basal petal spots*.—Basal petal spot, outermost petals: Outer Side: Yellow Group 2C. Inner Side: Yellow Group 13B. Basal petal spot, innermost petals: Outer Side: Yellow Group 13C. Inner Side: Yellow Group 13A.

*After opening, petals*.—Outermost petals: Outer Side: White Group 155C, with intonations of Red-Purple Group 62C in the marginal petal zone. Inner Side: Red-Purple Group 62C, with intonations of Red-Purple Group 61D in the middle and marginal petal zones. Innermost petals: Outer Side: White Group 155C. Inner Side: Red-Purple Group 61D, with a basal petal zone of White Group N155D.

*After opening, basal petal spots*.—Basal petal spot, outermost petals: Outer Side: Yellow Group 10B. Inner Side: Yellow Group 10A. Basal petal spot, innermost petals: Outer Side: Yellow Group 12B. Inner Side Yellow Group 12A.

General tonality: On open flower Red-Purple Group 61D. No change in the general tonality at the end of the second day. Afterwards, general tonality is Red-Purple Group 62C.

Petals:

*Petal count*.—Double.

*Average range*.—Approximately 25-30 petals under normal conditions.

*Petal reflex*.—Petals reflex somewhat strongly.

*Petal edge*.—With an indentation in the center.

*Petal shape*.—Round. Apex shape is round. Shape of base is rounded.

*Petal size*.—15-20 mm (l)×15-20 mm (w).

*Thickness*.—Thin.

*Petal arrangement*.—Not formal.

Petaloids:

*Petaloid count*.—Average of 4-8 per flower.

*Petaloid size*.—Petaloids are 15 mm (l) and 5 mm (w).

*Petaloid color*.—Color of inner side is. White Group 155C with intonations of Red-Purple Group N57C. Color of outer side is White Group 155C.

*Petaloid texture*.—Smooth.

*Margins*.—Undulated.

*Petaloid shape*.—Most commonly deltoid, with some petaloids highly irregular. Apex: Obtuse. Base: Attenuate.

Reproductive organs:

*Pistils*.—Average, approximately 25 present. Stigmas: Location: Slightly inferior in position to anthers. Color: Yellow-Green Group 144C. Styles: Length: About 5 mm long. Color: Yellow-Green Group 144D.

*Stamens*.—Approximately 50-60 on average and regularly arranged. Anthers: Size: Average 1 mm long.

Pollen: Generally present. Color: Greyed-Orange Group 163A. Filaments: Color: Yellow-Orange Group 22A. Length: 5-6 mm.

THE PLANT

Growth: Moderately vigorous.

Plant habit: Spreading habit. When grown as a budded field grown plant on *Rosa multiflora* understock the average plant height is 50 cm and the average plant width is 40 cm.

Blooming: Floriferous.

Stems:

*Stem color*.—Young wood: Yellow-Green Group 144A. Older wood: Yellow-Green Group 146D.

*Stem surface*.—Young wood: Smooth. Older wood: Smooth.

Prickles: Present.

*Incidence*.—Average of 7 per each 10 cm of stem.

*Size*.—Average length: 4 mm.

*Color*.—Immature prickles: Green-Yellow Group 160C. Mature prickles: Green-Yellow Group 161C. Intonations on mature prickles: Greyed-Red Group 182B.

*Shape*.—Deeply concave.

Leaves and leaflets: Normally 7 leaflets on normal leaves in middle of the stem.

*Venation pattern*.—Pyramidal net pattern.

*Leaf size*.—100 mm (l)×50 mm (w).

*Abundance*.—Average.

*Texture*.—Upper side of leaf: Semi glossy, smooth. Under side of leaf: Matte, smooth.

*Color, mature foliage*.—Upper Leaf Surface: Yellow-Green Group 146A. Lower Leaf Surface: Yellow-Green Group 146B.

*Color, juvenile foliage*.—Upper Leaf Surface: Green Group 137A. Lower Leaf Surface: Yellow-Green Group 146B.

*Anthocyanin intonation*.—Present on juvenile leaf margins, veins, and underside.

Stipules:

*Size*.—15 mm long, 5 mm from distal tip to distal tip.

*Stipule color*.—Yellow-Green Group 146C.

*Anthocyanin*.—Greyed-Red Group 182A and Greyed-Red Group 182B on the upper side.

*Margins*.—With stipitate glands.

*Shape*.—Apex: Apiculate. Base: Slightly winged.

Petiole:

*Length*.—Average 8-12 mm.

*Diameter*.—Average 1.5 mm.

*Petiole color*.—Yellow-Green Group 146C.

*Underneath*.—Prickles and stipitate glands.

*Margins*.—Pubescent with very few stipitate glands.

*Anthocyanin*.—Greyed-Red Group 182A on juvenile foliage.

Petiole rachis:

*Length*.—Average 10-15 mm.

*Diameter*.—Average 1 mm.

*Color*.—Yellow-Green Group 146C. Anthocyanin present on upper side, Greyed-Red Group 182A.

*Texture*.—Smooth underneath, with occasional prickles. Stipitate glands on margins.

Leaflets:

*Size*.—Average size of the terminal leaflet is 30 mm (l)×18 mm (w).

*Shape*.—Ovate. Base: Cuneate. Apex: Acute.

*Margins*.—Finely serrated.

*Surface*.—Upper: Semi glossy. Lower: Matte.

*Texture*.—Smooth.

*Arrangement*.—Odd pinnate

*Venation*.—Reticulate.

Hips/seed formation: Not observed.

Winter hardiness: To date, the variety has been grown successfully in USDA Zones 6-9.

Disease resistance: Excellent resistance to Powdery mildew (*Sphaerotheca pannosa*), blackspot (*Diplocarpon rosae*), and Botrytis (*Botrytis cinerea*) diseases under normal growing conditions.

I claim:

1. A new and distinct variety of rose plant, as described and illustrated herein.

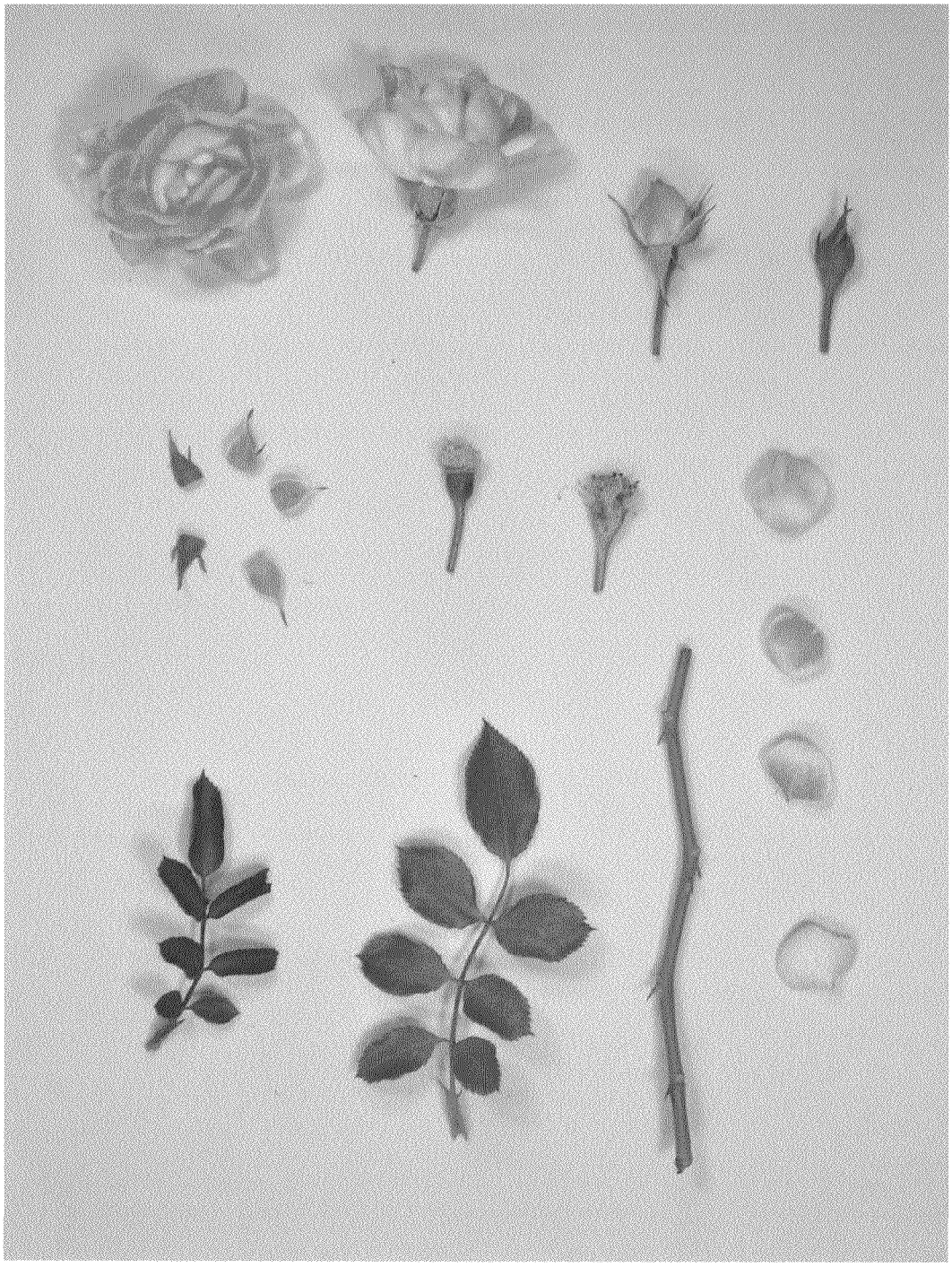

* * * * *